(12) United States Patent
Blendermann

(10) Patent No.: US 10,828,504 B2
(45) Date of Patent: Nov. 10, 2020

(54) WEARABLE DEVICE THAT INCREASES MUSCLE STRENGTH

(71) Applicant: Edward Ludwig Blendermann, Palm City, FL (US)

(72) Inventor: Edward Ludwig Blendermann, Palm City, FL (US)

(73) Assignee: Edward L. Blenderman, Palm City, FL (US)

( * ) Notice: Subject to any disclaimer, the term of this patent is extended or adjusted under 35 U.S.C. 154(b) by 0 days.

(21) Appl. No.: 16/350,193

(22) Filed: Oct. 12, 2018

(65) Prior Publication Data
US 2020/0114160 A1 Apr. 16, 2020

(51) Int. Cl.
| | | |
|---|---|---|
| *A61N 2/00* | (2006.01) | |
| *A61H 1/00* | (2006.01) | |
| *A61H 39/00* | (2006.01) | |
| *A61N 5/06* | (2006.01) | |
| *A44C 25/00* | (2006.01) | |

(52) U.S. Cl.
CPC ............ *A61N 2/002* (2013.01); *A44C 25/002* (2013.01); *A61H 1/008* (2013.01); *A61H 39/007* (2013.01); *A61N 2/004* (2013.01); *A61N 5/0613* (2013.01); *A61H 2201/165* (2013.01); *A61N 2005/0647* (2013.01)

(58) Field of Classification Search
CPC ...... A61M 2037/0007; A61M 37/0092; A61M 5/14248; A61M 2205/056; A61F 2007/0226; A61F 9/04; A61F 5/028; A61F 5/02; A63B 71/00; A63B 21/065; A63B 21/4009; A63B 21/4001; A61H 11/00; A61H 2201/10; A61K 9/7084; A61N 5/0619; A61N 1/36003; Y10S 2/11
See application file for complete search history.

(56) References Cited

U.S. PATENT DOCUMENTS

| | | | |
|---|---|---|---|
| 2003/0118615 A1* | 6/2003 | Blendermann ...... | A44C 25/002 424/400 |
| 2009/0234423 A1* | 9/2009 | Vetanze ............... | A61N 1/0408 607/88 |
| 2012/0144556 A1* | 6/2012 | Fiebel ................... | A41D 13/11 2/206 |
| 2013/0172829 A1* | 7/2013 | Badawi ................ | A61F 9/0008 604/294 |

(Continued)

OTHER PUBLICATIONS

Soleil Vie ("Algae spirulina, chlorella and klamath, what differences?", https://www.soleil-vie.com/fr_en/algae-spirulina-chlorella-and-klamatha-what-differences, Accessed online Feb. 10, 2020) (Year: 2020).*

*Primary Examiner* — Kaylee R Wilson

(57) ABSTRACT

An improvement on a method and device of the first wearable device that increases muscle strength using a holding device containing nutrients. This invention is detailed in U.S. Pat. Nos. 8,617,590, 9,636,310, 9,510,988. With the addition of a light source module and/or a vibrating module and/or a magnetic module to this holding device, it has been found that the resulting device has a surprising and unexpected synergistic effect on muscle strength. This phenomenal increase in muscle strength translates into improved athletic performance. The resulting holding device may be in the form of a belt, locket headband, wrist band, ankle band, pedal device, helmet, or gloves.

1 Claim, 21 Drawing Sheets

(56) References Cited

U.S. PATENT DOCUMENTS

| | | | |
|---|---|---|---|
| 2015/0105607 A1* | 4/2015 | Feng | A61N 2/008 600/13 |
| 2016/0213558 A1* | 7/2016 | Stanbridge | A61H 7/001 |
| 2018/0221683 A1* | 8/2018 | Kang | F21V 3/00 |
| 2018/0243580 A1* | 8/2018 | Verhoeks | A61N 5/0621 |
| 2019/0183724 A1* | 6/2019 | Sifferlin | A61H 23/0218 |

* cited by examiner

WEARABLE DEVICE THAT INCREASES MUSCLE STRENGTH

RELATED APPLICATIONS

The present application is an improvement over the nutrient holding devices as disclosed in U.S. Pat. Nos. 8,617,590, 9,636,310 and 9,510,988.

BACKGROUND

The present invention is an improvement over prior art wearable devices that increase muscle strength. Any device that can increase muscle strength has a utility that translates into improved athletic ability. Any improvement to this device to increase muscle strength has the utility of improving the ability of the device to increase muscle strength. A synergistic effect on increasing muscle strength that was both surprising and unexpected was discovered by using a light source module and/or a vibrating module and/or a magnetic module as an addition to the nutrient holding device described in the above patents to which this application is an improvement.

BRIEF SUMMARY OF THE INVENTION

This application documents the observation that the nutrient holding device in U.S. Pat. Nos. 8,617,590, 9,636,310 and 9,510,988 can increase a user's 1RM (1 Repetition Max the maximum weight a user can lift for 1 Repetition) from one repetition to two repetitions.

This application documents the discovery that a vibrating module added to the nutrient holding device increases muscle strength demonstrated by increasing the 1RM from 1 repetition to 3 repetitions. It also documents the discovery that the addition of a light module in combination with the nutrient holding device increases muscle strength from one repetition to three repetitions. This application documents the discovery that when both a vibrating module and a light source module are added to the nutrient holding device, there is a muscle strength increase as measured by the ability of a lifter to lift their 1RM up to four times. This application further documents the discovery that when a vibrating module, a light source module and a magnetic module are added to the nutrient holding device, there is a muscle strength increase as measured by the 1RM increasing from one repetition to five.

Incidentally, this application also documents the discovery of a vibrating module alone in a holding device can increase the 1RM from one repetition to two.

Incidentally, this application also documents the discovery that a light source module alone directing the rays toward the skin can increase the 1RM from one repetition to two repetitions.

Incidentally, this application documents the discovery that a magnetic module held in a holding device can increase the 1RM from one repetition to two.

Incidentally, this application also documents the discovery of a holding device containing a vibrating module and a light source module directing its rays toward the skin can increase the 1RM from one repetition to three repetitions.

Incidentally, this application documents that a holding device containing a magnetic module and a light source module directing the rays toward the skin can increase the 1 RM from one repetition to three.

Incidentally, this application documents the discovery that a magnetic module and a vibrating module in a holding device will increase the 1RM from one repetition to three.

Incidentally, this application documents the discovery that a holding device containing a magnetic module, a light source module and a vibrating module will increase the 1RM from one repetition to four.

These discoveries that improve muscle strength have led to an improved nutrient holding device because of the improved utility of the device to increase muscle strength when the vibrating module and/or the light source module and/or magnetic module is incorporated into the holding device.

DESCRIPTION OF DRAWINGS

FIGS. 1-21 illustrate a simple holding device which is in the form of a belt. It may be attached at various locations of the body to achieve the utility of increased muscle strength.

FIG. 1 illustrates an example of the nutrient holding device of which this invention will be an improvement thereof. The holding device preferably includes hook-and-loop fasteners Velcro™ or the like; hereafter "fasteners") which provide a means of attaching this elastic belt (2) snuggly around various surfaces of the body allowing the nutrients (4) to be held next to the body in a waterproof compartment (3) as patented in U.S. Pat. No. 8,617,590. This belt allows the user to increase his 1RP by one to 2 repetitions.

FIG. 2 B Illustrates a posterior view of the above belt showing a power battery pack (6) which may be rechargeable and an ON/OFF switch (3). The power pack (6) supplies the light source module (5) with power. The light source module is not shown in this view.

FIG. 3 A illustrates an anterior view (adjacent to skin) holding device in the form of an elastic belt (2) with fasteners ends (1) which houses a vibrating module (8) which may be used independently to increase muscle strength. This belt increases the 1RM by 1 repetition to 2 repetitions. The fasteners ends (1) along with varying the length of the belt allows the belt to be adjusted so that it can be attached to various locations including the wrist, waist head, upper back, mid back, lower back, ankle leg, arm and abdominal or thorax regions. The multiple placement of the device is permitted by the abundance of mechanoreceptors that can be stimulated on the skin balancing acupuncture points resulting in increased muscle strength.

FIG. 4 A illustrates an anterior view (adjacent to the skin) of similar belt (2) to FIG. 1 but with the addition of a light source module (5) that directs the rays toward the skin. This belt has a waterproof compartment (3) containing nutrients (4) but with the addition of the light source module (5) represents an improvement to the nutrient holding device (FIG. 1) and has a synergistic effect on muscle strength in that it can increase the ability of the invention to do another repetition. This allows the 1RM to be increased by 2 repetitions to three repetitions.

FIG. 5 A illustrates an anterior view (adjacent to the skin) of similar belt (2) to FIG. 1 with the addition of a vibrating module (8). This belt (2) has a waterproof compartment (3) containing nutrients (4) but with addition of the vibrating module (8) represents an improvement to the nutrient holding device (FIG. 1) and has a synergistic effect on increasing muscle strength in that it can now increase the ability of the invention to do another repetition. This allows the 1RM to be increased by two repetitions to three repetitions. The fastener ends (1) are used as convenient attachments so that the belt with different lengths can be used at various locations including the ankles, wrist (wrist band), forehead (head band or fashioned into a helmet or hat), waist (fashioned into athletic wear or a belt), arms, legs, chest, and back.

FIG. 6 A illustrates an anterior view (adjacent to the skin) of similar belt to FIG. 1 but with the addition of both a light source module (5) and a vibrating module (8). This belt (2) also has a waterproof compartment (3) containing nutrients (4). It represents an improvement to the nutrient holding device (FIG. 1) with the addition of the light source module (5) and the vibrating module (8). This causes a synergistic effect of increasing the muscle strength so that the 1RM is increased by 3 repetitions to 4 repetitions. The fastener ends (1) are also illustrated.

FIG. 8 This is an illustration of cross sectional view of a light source module (5) that shows the light emitting diode (LED) lights (11) that are directed toward the skin so that they may stimulate the abundance of mechanoreceptors that when balanced cause an increase in muscle strength. Also illustrated are the power source that is a battery pack (6) and on/off switch (7) located on top of the light module (1). A portion of the elastic belt (2) is also shown.

FIG. 9 is a cross sectional view of a vibrating module (8) that depicts a vibrating motor (12). The power source that is a battery pack (9) and on/off switch (10) are located on top of the vibrating module (8). A portion of the elastic belt (2) is also shown.

FIG. 12 is an anterior view of an elastic belt (2). The magnetic module (16) is held next to the body by this elastic belt (2) with fastener ends (1) allowing for convenient adjusting of the length of the belt.

FIG. 13 is an anterior view of an elastic belt (2). The magnetic module (16) is depicted alongside a waterproof compartment (3) containing nutrients (4). The elastic belt securely holds the nutrient holding compartment (3) and the magnetic module (16) next to the skin. The fastener ends (1) are also shown.

FIG. 14 A is an anterior view of an elastic belt (2). The magnetic module (16) is depicted alongside the light source module (5). The elastic belt (2) securely holds the magnetic module (16) and the light module (3) next to the skin. The fastener ends (1) are also shown.

DETAILED DESCRIPTION OF INVENTION

Figure 1:
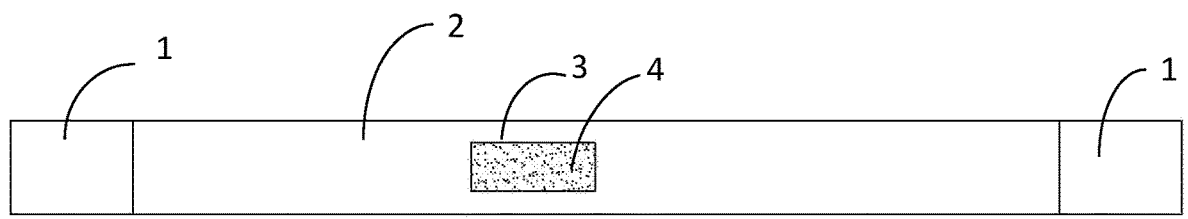
Figure 2A:
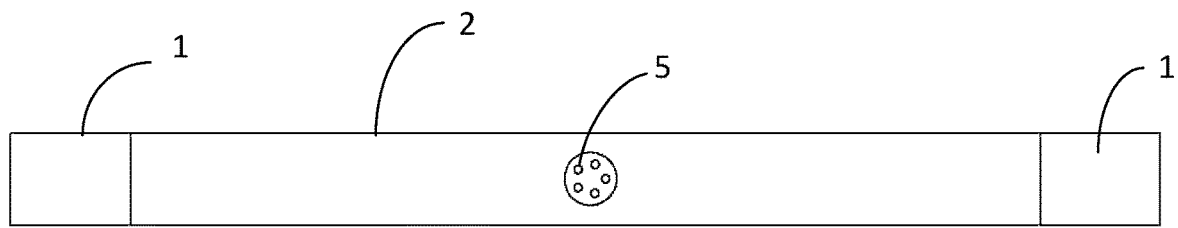
FIG. 2A illustrates an anterior view (adjacent to the skin) of an example of a holding device in the form of an elastic belt (2) with fasteners ends (1) housing a light source module (5) which may be used independently to increase muscle strength. The rays of the light source will be directed toward the skin where an abundance of mechanoreceptors can be stimulated balancing acupuncture points resulting in increased muscle strength. This belt can increase the 1RP by one repetition to two repetitions.
Figure 2B:
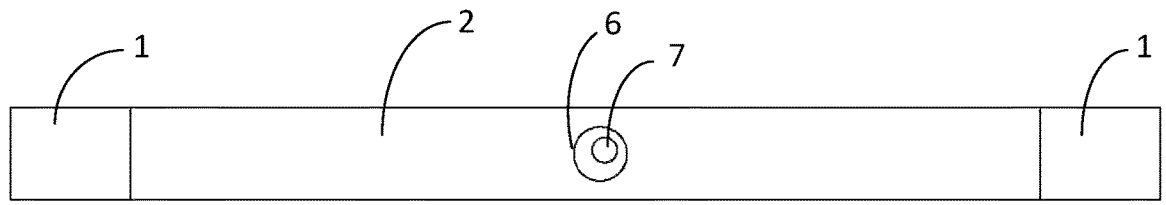
Figure 3A:
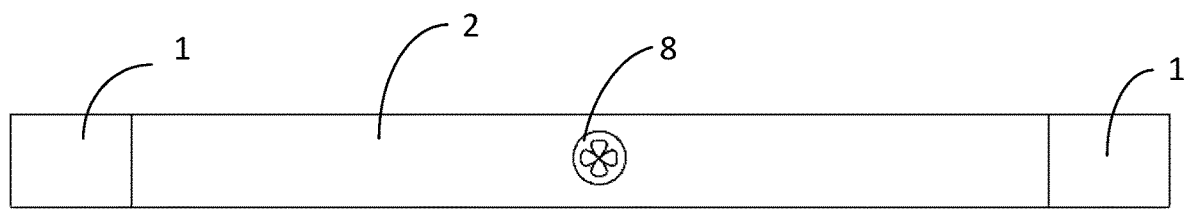
Figure 3B:
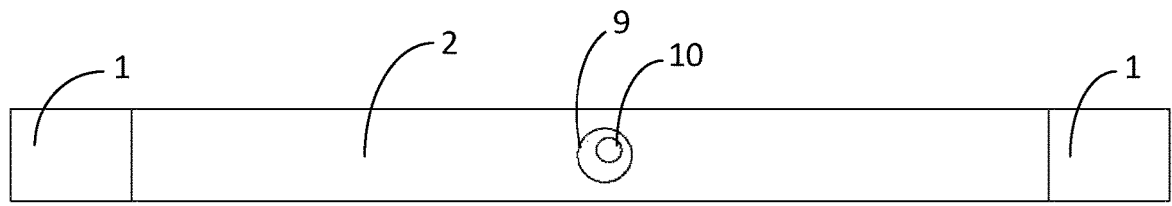
FIG. 3B illustrates a posterior view of the above belt (2) showing the power pack (9) (battery pack which may be rechargeable) and an ON/OFF switch (10). The power pack (9) supplies power to the vibrating module (not shown). The fastener ends (1) are depicted.
Figure 4A:
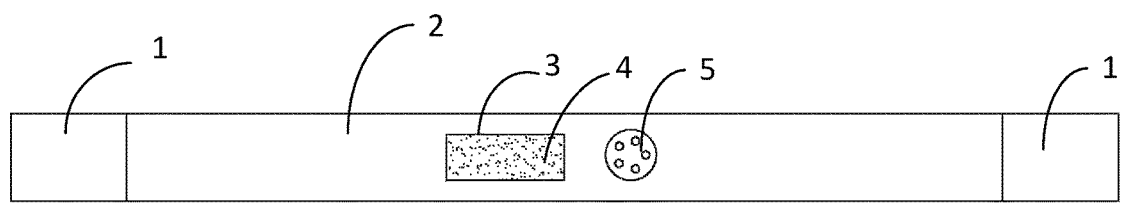
Figure 4B:
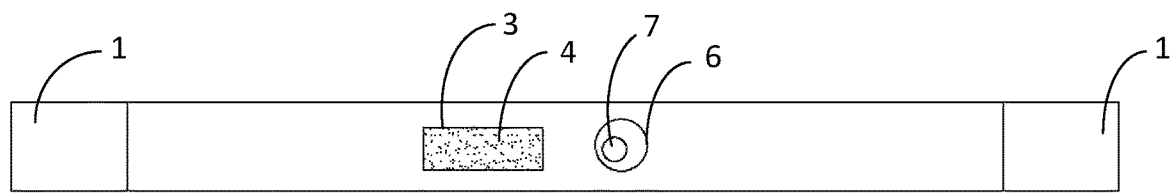
FIG. 4B illustrates a posterior view of the belt above (2). The power pack (6) (a battery pack which may be rechargeable) is shown with an ON/OFF switch (7). The power pack (6) supplies power to the light module (not shown). The waterproof housing of the compartment (3) containing the nutrients (4) is shown. The fastener ends (1) are depicted.
Figure 5A:
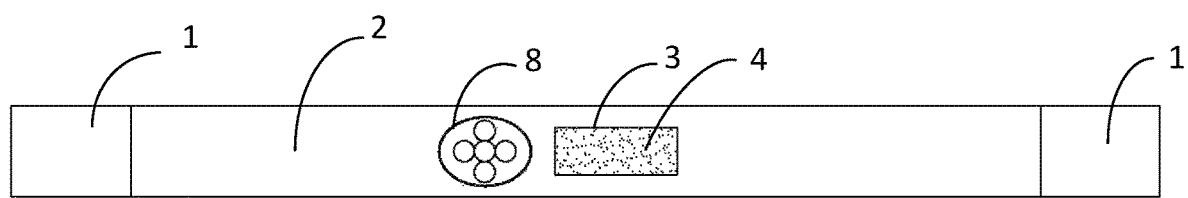
Figure 5B:
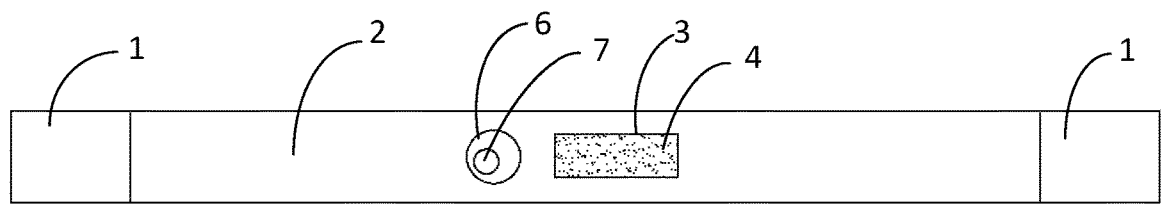
FIG. 5B illustrates a posterior view of the above belt (2). The power pack (9) (a battery pack which may be rechargeable) is shown with an on/off switch (10). The power pack (9) supplies power to the vibrating module (not shown).
Figure 6A:
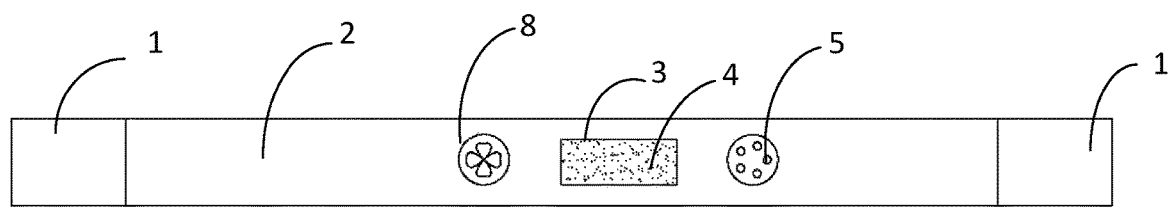
Figure 6B:
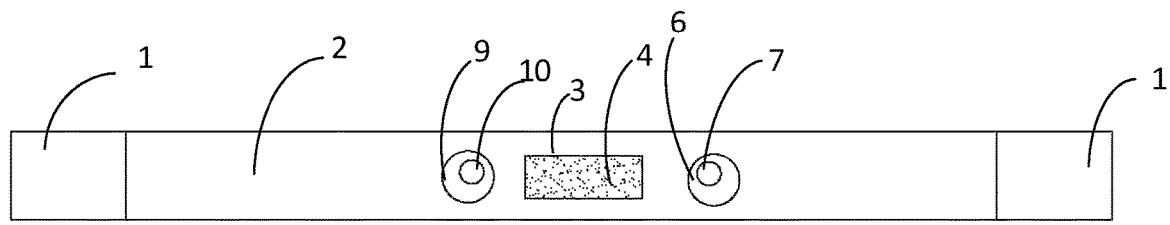
FIG. 6B illustrates a posterior view of the above belt (2). The power packs (6, 9) (battery pack which may be rechargeable) sit on top of the light source module (not shown) and the vibrating module (not shown). An On/Off switches (7, 10) are depicted on top of each module. The waterproof compartment (3) of the nutrients (4) are also shown. The fastener ends (1) are depicted.
Figure 7A:
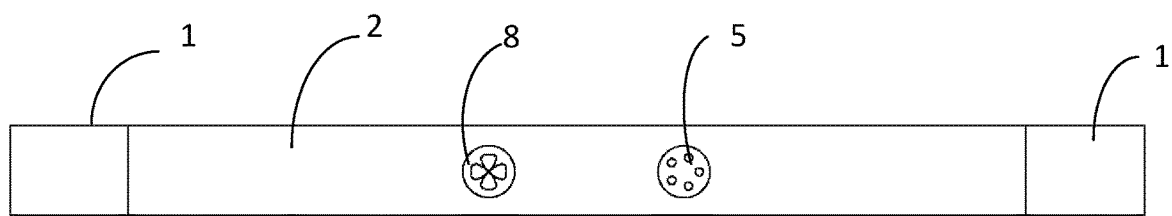
FIG. 7A illustrates an anterior view (adjacent to the skin) of an elastic belt (2) holding a vibrating module (8) and a light source module (5). Both of these modules have a synergistic effect on each other. one repetition max by two repetitions to three repetitions. The fastener ends (1) are also illustrated.
Figure 7B:
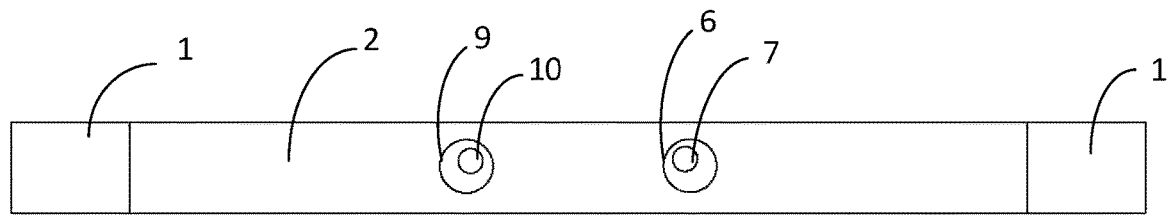
FIG. 7B shows a posterior view of the above elastic belt (2). The power packs (2) may preferably be battery packs or the like (which may be rechargeable) and may include an ON/OFF switch which may sit (3) on top of both the light source module and the vibrating module to which they supply power. The fastener ends (1) are also illustrated.
Figure 8:
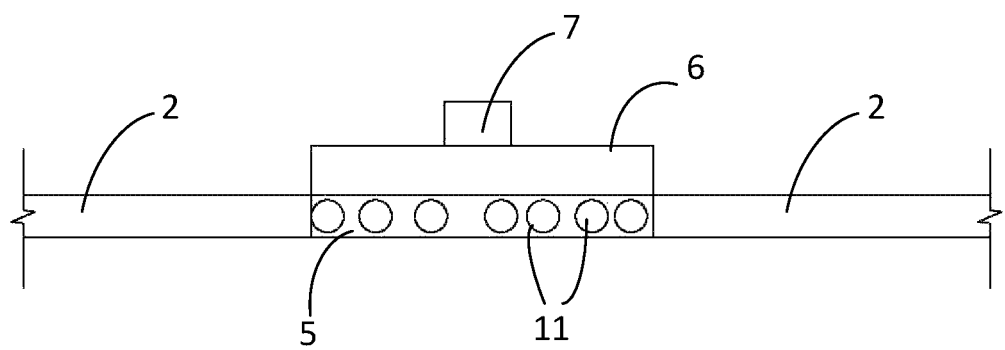
Figure 9:
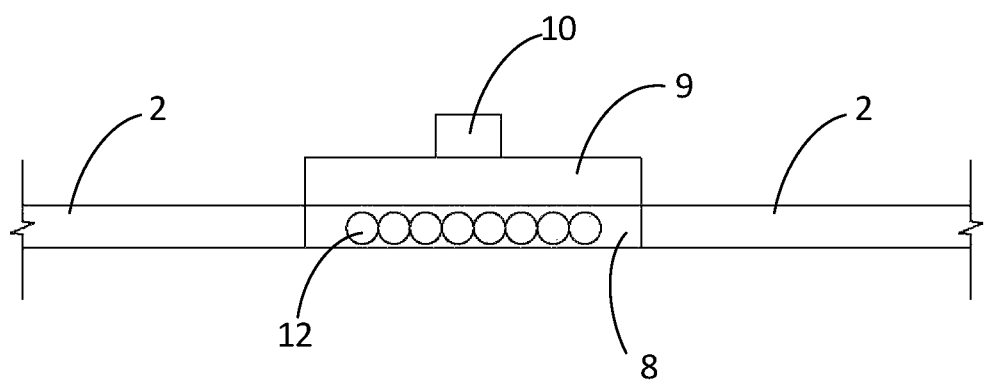
Figure 10A:
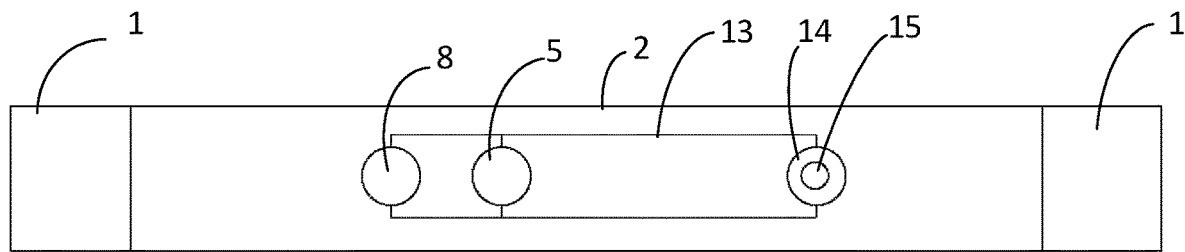
FIG. 10A is a posterior elastic belt (2) that has a power pack (14) (battery pack) so that the power source can be distal to the light source (5) and/or vibrating module (8). The on/off switch (15) is located on top of the power pack (14). The electrical connections (13) from the power pack (14) to the light module (5) and vibrating module (8) are also illustrated. The fastener ends (1) are also depicted.
Figure 10B:
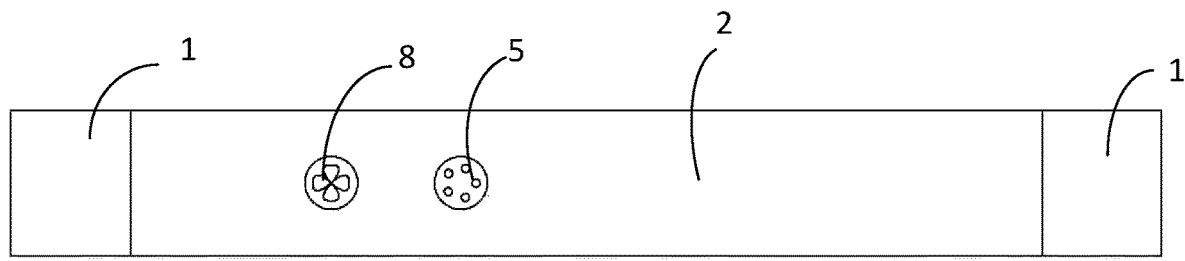
FIG. 10B is an anterior view of the above elastic belt (2). This view shows the side of the belt adjacent to the skin. The location of the vibrating module (2) is shown. Also shown is the location of the light module (3). The fastener ends (1) are also depicted.
Figure 11A:
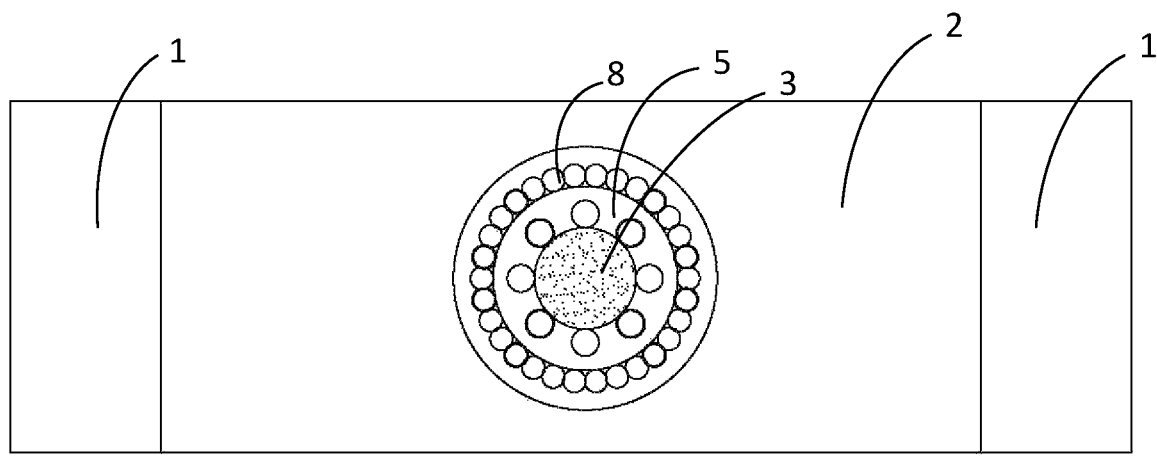
FIG. 11A is an anterior view of an elastic belt (2) with a vibrating module (8), together with a light module (5) surrounding the waterproof compartment (3) that contains nutrients (4). The fastener ends (1) are also depicted. This anterior view is adjacent to the skin when worn.
Figure 11B:
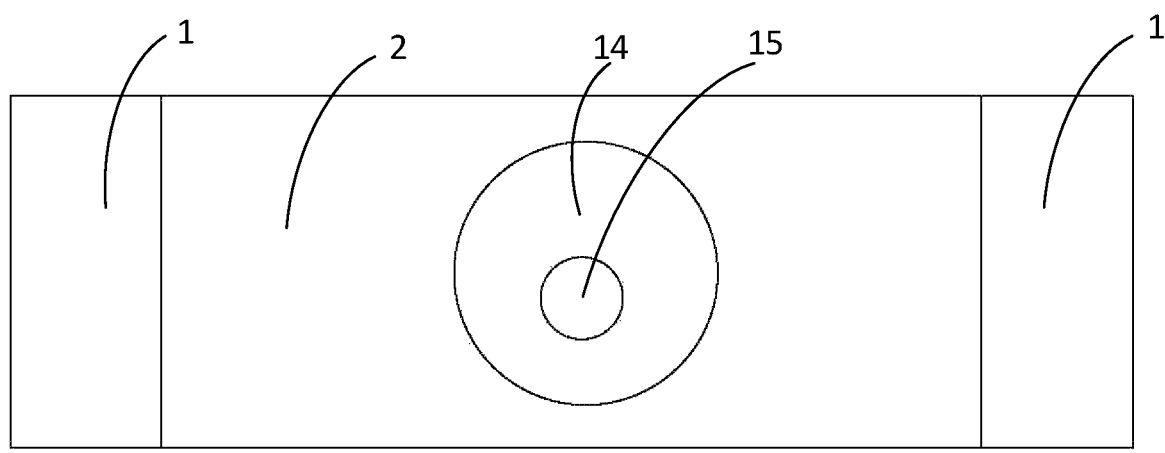
FIG. 11B is a posterior view of the above elastic belt (2). The power pack (14) is shown on which sits an on/off switch (15). The fastener ends (1) are also depicted.
Figure 11C:
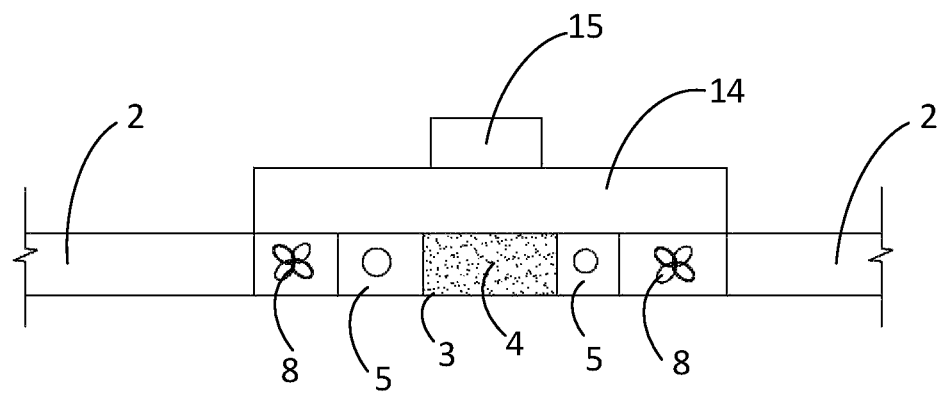
FIG. 11C is a cross sectional view of the above belt (2). The power pack (14) is shown on which sits the on/off switch (15). The vibrating module (8) surrounds the light module (5) which surrounds the waterproof compartment (3) containing the nutrients (4).
Figure 12:
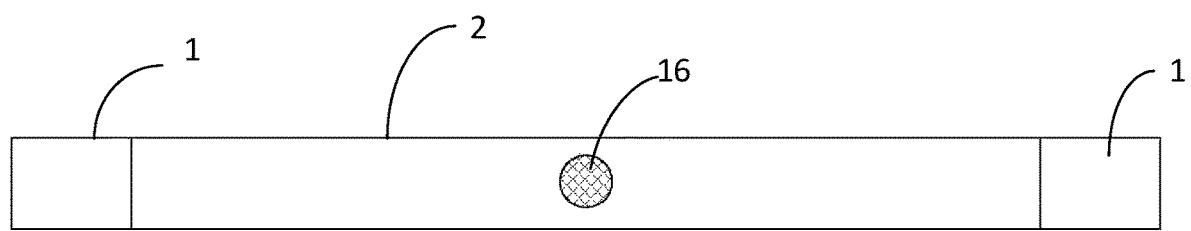
Figure 13:
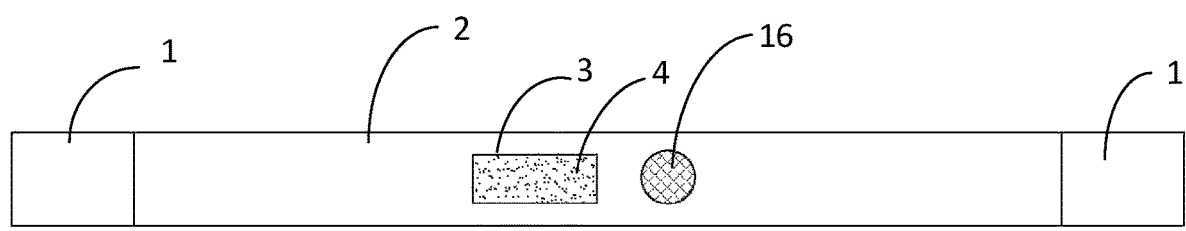
Figure 14A:
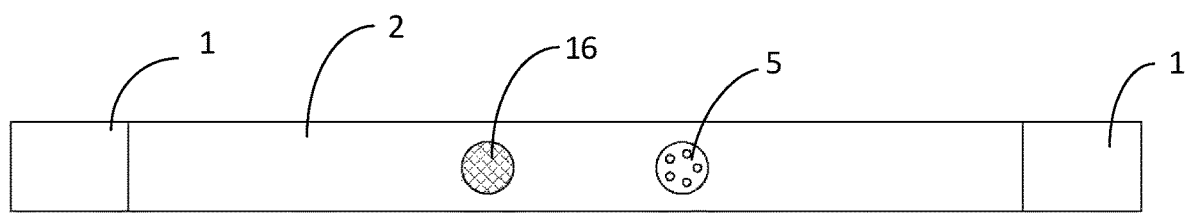
Figure 14B:
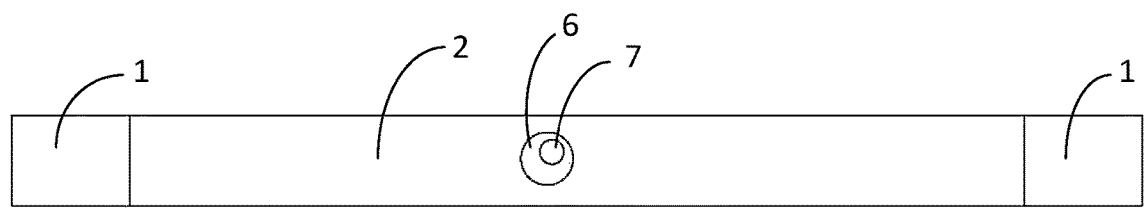
FIG. 14B is a posterior view of the above belt (2). A battery pack (6) which may be rechargeable is depicted along with an ON/OFF switch (7). The magnetic module seen on the anterior view is not shown.
Figure 15A:
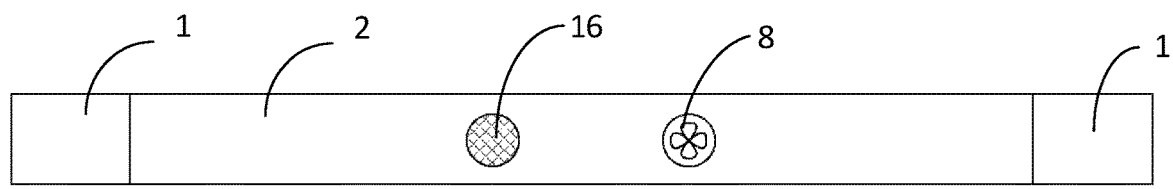
FIG. 15A This illustration shows an anterior view of an elastic belt (2). It also depicts a magnetic module (16) shown next to a vibrating module (8). The elastic belt (2) holds the magnetic module (16) and the vibrating module (8) next to the skin. The fastener ends (1) are also shown.
Figure 15B:
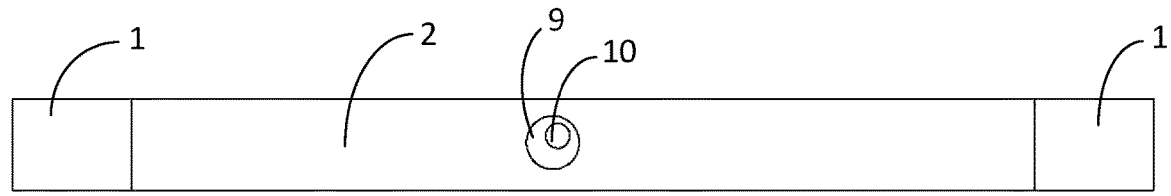
FIG. 15B is a posterior view of the above belt (2). It depicts a battery pack (9) which may be rechargeable and an ON/OFF switch (10). The fastener ends (1) are also shown. The magnetic module is not shown in this view.
Figure 16A:
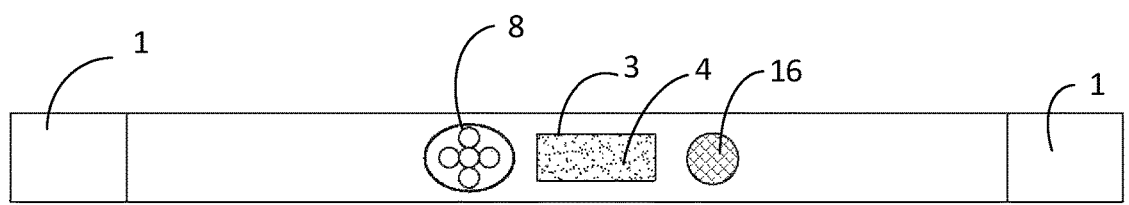
FIG. 16A is an anterior view of view of an elastic belt (2). The vibrating module (8), the waterproof compartment (3) containing nutrients (4) and the magnetic module (16) are held next to the skin by the elastic belt (2) with its fastener ends (1).
Figure 16B:
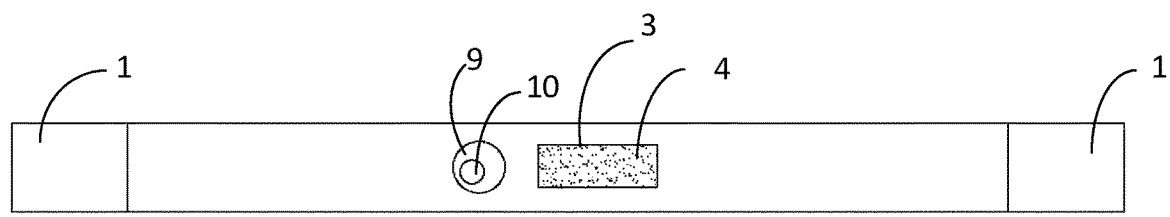
FIG. 16B is a posterior view of the above elastic belt (2). The fastener ends 1) are shown and the battery pack (9) is shown. The ON/OFF (10) switch is also depicted. The waterproof compartment (3) containing nutrients (4) is shown. In this view the magnetic module is not shown.
Figure 17A:
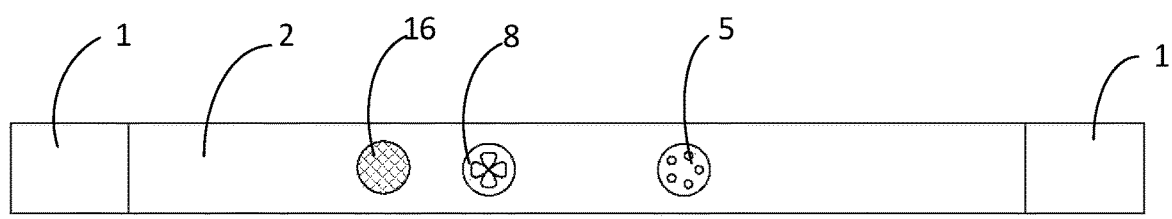
FIG. 17A is an anterior view of an elastic belt (2). The fastener ends (1) are shown. The magnetic module (16), the vibrating module (8) and the light source module (5) are held close to the skin by this elastic belt (2).
Figure 17B:
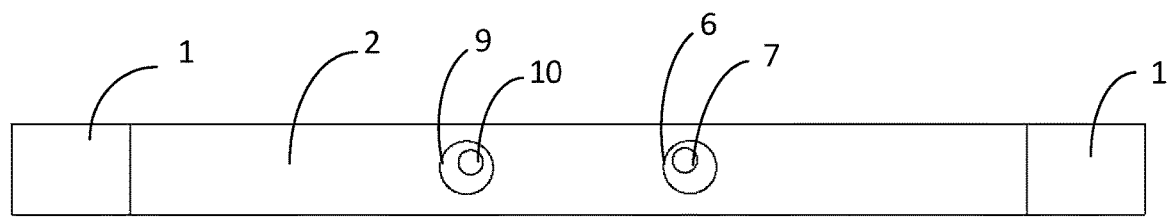
FIG. 17B is a posterior view of the above elastic belt (2). Two powerpacks (6, 9) with respective ON/OFF switches (7,10) are shown for powering the light source module (5) and the vibrating module (8) respectively.
Figure 18A:
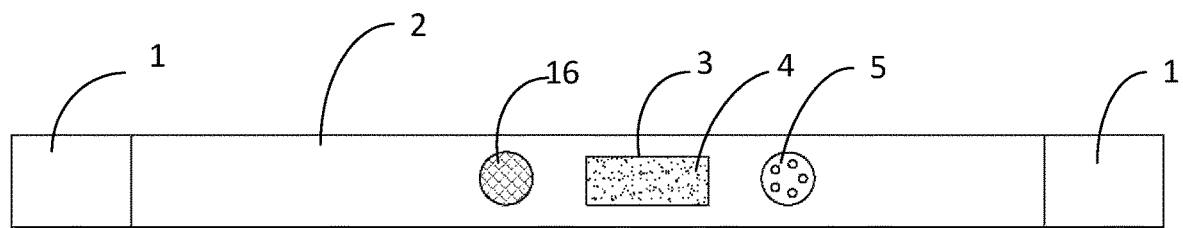
FIG. 18A is an anterior view of an elastic belt (2). The magnetic module (16), the waterproof chamber (3) holding the nutrients (4), and the light source module (5) are shown. The elastic belt (2) holds the magnetic module (16), the waterproof compartment (3) holding the nutrients (4), and the light source module (5) next to the skin. The fastener ends (1) are shown.
Figure 18B:
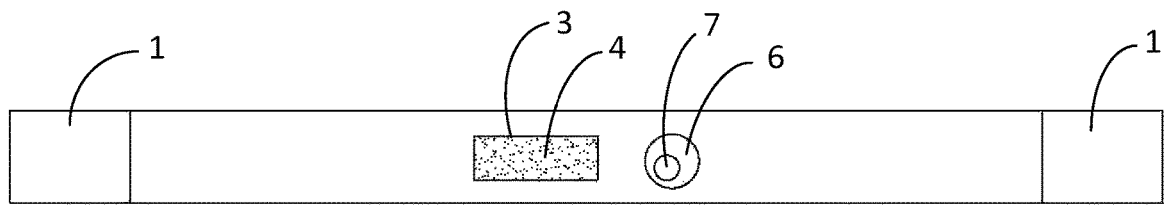
FIG. 18B This is a posterior view of the above elastic belt (2). The fastener ends (1) are shown. The waterproof housing (4) containing the nutrients (4) is depicted. The battery pack (6) and the ON/OFF switch (7) powering the light source module (not shown on this view) are illustrated.
Figure 19A:
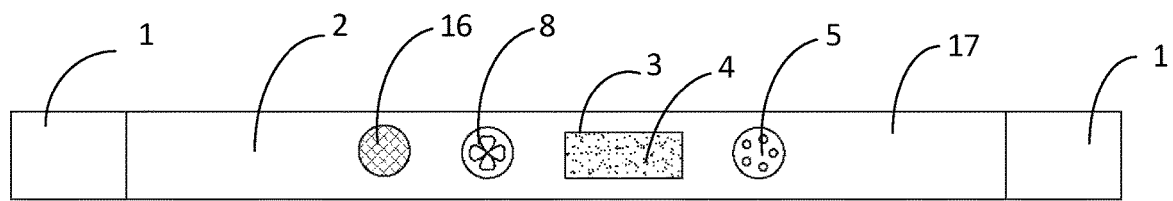
FIG. 19A is an anterior view of an elastic belt (2) showing the inside surface (17) of the elastic belt (2). This inside surface (17) is the user facing side when the fastener ends (1) are connected and the belt is worn by a user. The magnetic module (16) is shown. The vibrating module (8) is shown. The waterproof housing (3) containing the nutrients (4) is depicted. The light source module (5) is illustrated. The elastic belt (2) holds these components next to the skin.
Figure 19B:
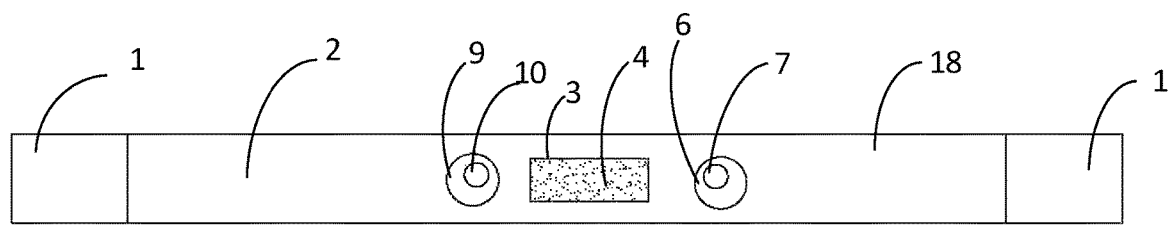
FIG. 19B is a posterior view of the above elastic belt (2) showing the outside surface (18) of the elastic belt (2). This outside surface (18) is understood to face away from the user when the fastener ends (1) are connected and the belt is worn by a user. Two power packs (6, 9) with respective ON/OFF switches (7,10) are shown for powering the light source module (5) and the vibrating module (8). Between them is shown the waterproof compartment (3) containing the nutrients (4)
Figure 20A:
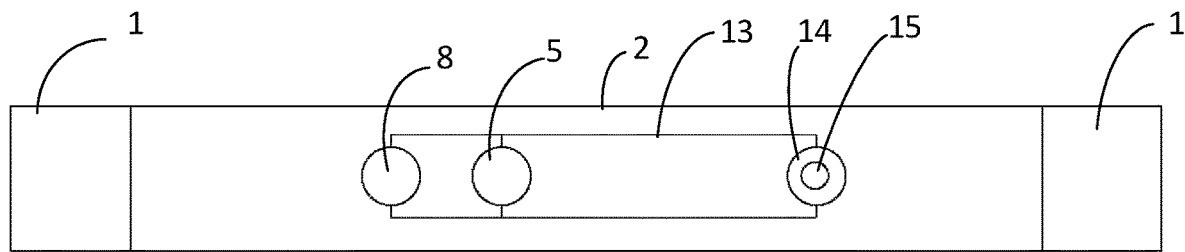
FIG. 20A is a posterior view of an elastic belt (2). This belt has a magnetic module which is not shown in this view. This view shows a power pack (14) and an ON/Off switch (15). It shows the electrical connections (13) from the power pack (14) to the light source module (5) and vibrating module (8). The purpose of this illustration is to show that the light source module (5) and the vibrating module (8) may have the same power source (14).
Figure 20B:
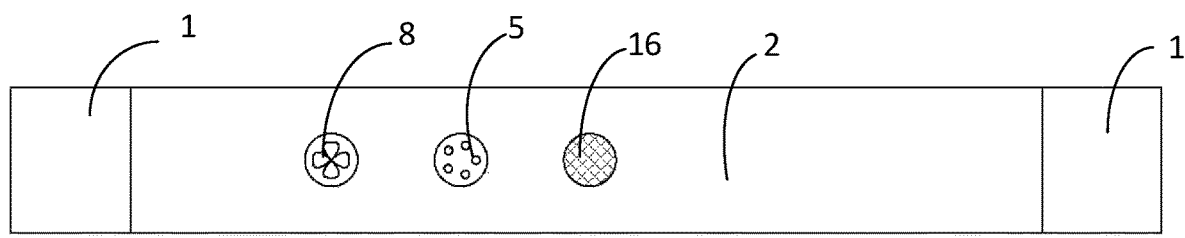
FIG. 20B This illustrates the above elastic belt (2) in an anterior view. The vibrating module (8) is shown. The light source module (5) is shown as well as a magnetic module (16). These three modules are held next to the skin by the elastic belt (2). The fastener ends (1) are also depicted.
Figure 21A:
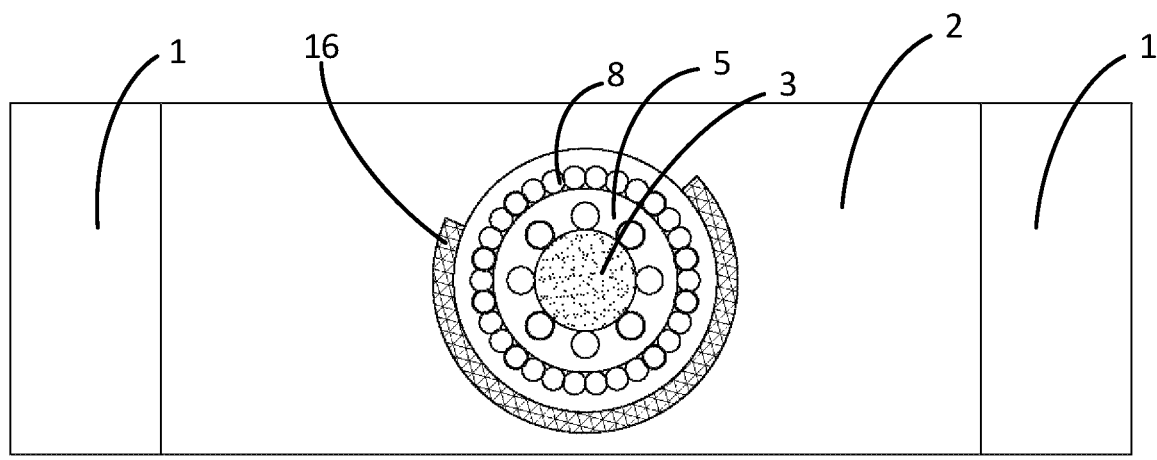
FIG. 21A is an anterior view of an elastic belt (2) with a vibrating module (8), together with a light module (5) surrounding a waterproof compartment (3) that contains nutrients (4). A ring like magnetic module (16) surrounds the entire device (note the upper part of the ring has been left out so as not to interfere with markings of this illustration). The fastener ends (1) are shown. This anterior view is adjacent to the skin when worn.
Figure 21B:
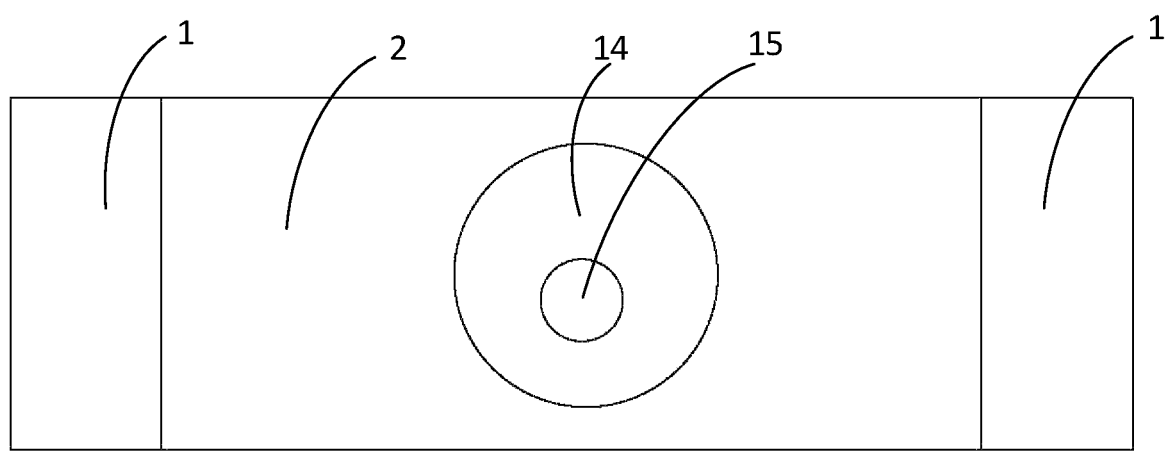
FIG. 21B is a posterior view of the above elastic belt (2). The power pack (14) is shown on which sits an ON/OFF switch (15). The fastener ends (1) are also shown.
Figure 21C:
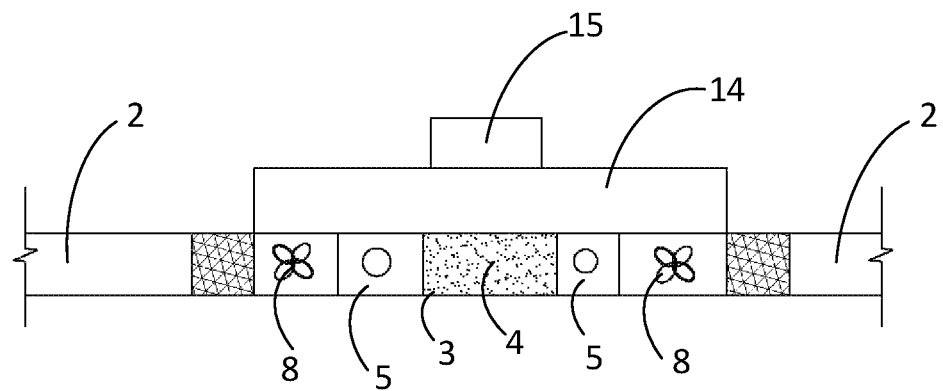
FIG. 21C is a cross sectional view of the above elastic belt (2). The power pack (14) is shown on which sits the ON/OFF switch (15). The vibrating module (8) surrounds the light module (5) which surrounds the waterproof compartment (3) containing nutrients (4). The entire device is surrounded by a ring-like magnetic module (16).

It has been discovered that the addition of a light source directed toward the body to the various holding devices in U.S. Pat. Nos. 8,617,590, 9,636,310, 9,510,988 (which are hereby incorporated by reference herein in their entirety) has an unexpected and surprising synergistic effect on the ability of the device to increase muscle strength.

Likewise, it has been discovered that the addition of a vibrating module to the holding devices in U.S. Pat. Nos. 8,617,590, 9,636,310, 9,510,988 has an unexpected and a surprising synergistic effect on the ability of the device to increase muscle strength.

In addition, it has been discovered that the addition of a magnetic module to the nutrient holding device has an unexpected and surprising synergistic effect on the ability of the device to increase muscle strength.

The theory behind U.S. Pat. Nos. 8,617,590, 9,636,310, 9,510,988 is that the stimulation of mechanoreceptors, which is how acupuncture points are balanced, results in strengthening of muscles. In U.S. Pat. Nos. 8,617,590, 9,636,310, 9,510,988, electromagnetic waves (EMWs) from nutrients stimulate mechanoreceptors.

Peter Mandel, a renowned acupuncturist suggested that the resultant cellular changes caused by light can affect the electrical receptivity of related acupuncture points on the surface of the skin.

Acupuncture points may be balanced using light. This led to the hypothesis that if light could balance acupuncture points and balanced acupuncture points result in increased muscle strength, then a light source module could affect muscle strength if added to the holding devices in U.S. Pat. Nos. 8,617,590, 9,636,310, 9,510,988.

Also, acupuncture points may be balanced by acupressure. This led to the hypothesis that mechanical vibration from a vibrating module might stimulate mechanoreceptors that would balance acupuncture points resulting in increased muscle strength.

In addition, magnetism has been used to balance acupuncture points. This led to the hypothesis that a magnetic module could be used in a holding device to increase muscle strength.

To reiterate the means of increasing muscle strength in U.S. Pat. Nos. 8,617,590, 9,636,310, 9,510,988 are electromagnetic waves from nutrients that stimulate mechanoreceptors which balances acupuncture points which results in increased muscle strength.

This invention is an improvement of this wearable device because of the addition of the light source and/or vibrating module and/or a magnetic module which also balance acupuncture points and can likewise increase muscle strength. These improvements to U.S. Pat. Nos. 861,750, 9,636,310, 9,510,988 (the first wearable device that increases muscle strength) are that both the light source module and the vibrating module and/or the magnetic module improve the ability of the holding device to increase muscle strength. This increase in strength translates into improved athletic ability whether lifting weights or performing other athletic activities.

The use of the term 1RM will be used in the proof of the utility of the present invention. The definition of 1RM in weight training (Wikipedia) is "the maximum amount of weight a person can possibly lift for one repetition . . . . One repetition maximum can be used for determining an individual's maximum strength and is the method for determining the winner in events such as powerlifting and weightlifting competitions." In other words, if a subject believes his 1RM is 200 lbs. on a bench press he can lift this weight once. On the second attempt to do this press he would fail. Also, if he would add 5 lbs to his 1RM he would not be able to press the amount.

As will be shown the ability to increase the one repetition max from one repetition to two has been observed by using the nutrient holding device patented in U.S. Pat. No. 8,617, 590. When the nutrient holding device is used with a light source module the 1RM is increased from one repetition to three. When the nutrient holding device is used with the vibrating module, the 1RM is increased from one repetition to three. When the nutrient holding device is used with the magnetic module, the 1RM is increased from one repetition to three.

And when the nutrient holding device is used with both the light source module and the vibrating module the 1RP increases from one repetition to four. Similarly, when the nutrient holding device is used with both the magnetic module and the light source holding device, the 1RM is increased from one repetition to four. Likewise when the nutrient holding device is used with the magnet module and the vibrating module the 1RM is increased from one repetition to four. Finally, when the nutrient holding device is used with the vibrating module, the light source module and the magnetic module, the 1RM is increased from one repetition to five.

When synergistic agents work together, they accomplish more than they could alone. When used together in a holding device the nutrients, vibrating module, magnetic module, and light module produce a better final outcome on increasing muscle strength when working together than when working separately.

Investigation into the hypothesis that a light module could increase the 1RM when used separately:

A light module that can be described as an LED light source (full spectrum visible white light) that directs its beam toward the skin at the umbilicus or the solar plexus has been used successfully to increase the 1RM by 5 lbs.

A subject determines his 1RM on a bench press. (he can lift the weight one time but only one time) He lifts his one repetition maximum. He rests 5 minutes. He adds 5 lbs. to the weight. He tries to lift it. He cannot. He tries 3 times with 10 seconds apart. He still fails. Now he turns on a switch which turns on the light module with rays set on the umbilicus. Immediately he attempts to lift the 1RM plus 5 lbs. He is successful.

This scenario is repeated on the triceps press: a subject determines his 1RM. He adds 5 lbs. He fails to lift the weight. He tries 3 times with 10 seconds apart. He still fails. After turning on the light module with rays directed toward the umbilicus, he immediately can lift the 1RM plus 5lbs one time.

This scenario is repeated using the leg press: a subject determines his 1RM. He adds 5 lbs. He cannot move the weight. He tries 3 times with 10 seconds apart. Still he fails to move the weight. He then turns on the light module with rays directed toward the umbilicus. Immediately, he is successful in lifting the weight one time.

The above three scenarios are repeated. This time the light module is moved to the solar plexus. The same results of being able to lift the 1RM plus 5 lbs. is achieved.

The above scenarios were repeated moving the modalities to the upper back, lower back, mid back, arms, wrist, head, and feet. The same results of being able to lift 1RM plus 5 lbs. was achieved at these different locations. Since mechanoreceptors are located all over the body when they are stimulated, they may balance acupuncture points resulting in increased muscle strength. This allows for multiple areas where the device may be placed to perform the utility of increased muscle strength.

Investigation into the hypothesis that a vibrating module can increase the 1RM when used separately:

A subject determines his 1RM on a bench press (he can lift the weight one time but only one time) He rests 5 minutes. He then adds 5 lbs. to the weight. He tries to lift it. He cannot. He tries 3 times with 10 seconds between each attempt. Still he fails to lift the weight. Now he turns on a switch which activates a vibrating module set on the umbilicus. Immediately he can lift the weight one time.

The scenario is repeated using a triceps press: a subject determines his 1RM on a triceps press. He rests 5 minutes. He then adds 5 lbs. to his 1RM. He attempts to lift he weight. He cannot. He tries to lift the weight 3 more times with 10 seconds between each attempt. Still he cannot move the weight. Now he turns on a switch which activates a vibrating module on his umbilicus. Immediately he is able to lift the weight one time.

The scenario is repeated. This time the exercise used is a leg press. The subject determines his 1RM. He rests 5 minutes. He then adds 5 lbs. to his 1RM. He tries to lift he weight. He cannot. He tries 3 more times with 10 seconds between each attempt. He still cannot lift the weight. He then turns on a switch which activates the vibrating module located on the umbilicus. He immediately can lift this weight one time.

The above three scenarios are repeated. This time the vibrating module is moved to the solar plexus. The same results of being able to lift the 1RM plus 5 lbs. one time is achieved.

The scenarios were repeated. This time moving the device to the lower back, mid back, legs, arms, feet, and wrists, and also the head. The same results of being able to lift 1RP plus 5 lbs was achieved. Since mechanoreceptors are located all over the surface of the body and their stimulation results in balanced acupuncture points the multiple placements of the device on the body can still produce the desired effect of increasing muscle strength.

Examination into using the magnetic module alone on increasing muscle strength:

The magnetic module is a powerful magnet (14600 Gauss) that may be attached to a holding device which secures the magnet next to the skin at various locations where it balances acupuncture points resulting in increased muscle strength.

A subject determines his 1Rm on a bench press. (he can lift the weight one time but only onetime, on the second attempt he fails). The subject lifts his 1RM. He rests 5 minutes. He then adds 5 lbs. to the weight. He tries to lift it. He cannot. He tries three times with 10 seconds between each attempt. He still fails. He then puts on the magnetic module which he places under a belt located just below the umbilicus. He can now lift his 1RM plus 5 lbs. one time.

This scenario is repeated using the triceps press: A subject determines his one repetition max. He adds 5 lbs. He attempts to lift the weight. He cannot. He tries three times with 10 seconds between each attempt. He cannot lift the weight. He then puts the magnetic module under a belt allowing the magnetic module to rest just below the umbilicus. Immediately, he can now lift his 1RM plus 5 lbs. one time.

The Scenario is repeated this time using a leg press: A subject determines his 1RM. He adds 5 lbs. He cannot move the weight. He tries 3 times with 10 seconds between each attempt. Still he fails to lift the weight. He then puts the magnetic module under a belt allowing the magnetic module to rest just below the umbilicus. He immediately can lift his 1RM plus 5 lbs. one time.

The above three scenarios are repeated. This time the magnetic module is moved to the solar plexus the upper back, the lower back, the mid back, each arm, each wrist, the forehead, the head, the feet and ankles. The same result of being able to lift the 1RM plus 5 lbs is achieved. Since acupuncture points are located all over the surface of the body and when they are balanced by a magnetic field, the result is an increase in muscle strength.

Examination of the synergistic effect of the nutrients (U.S. Pat. Nos. 8,617,590, 9,636,310, 9,510,988), light module, magnetic module and vibrating module being used 0 her has led to the utility of this invention that is increasing the ability of the nutrient holding device to increase muscle strength. This discovery was surprising and unexpected which will be explained as follows:

A subject determined his 1RM on a bench press. (he was able to press the weight one time but only one time) He rested 5 minutes. Then he added 5 lbs to the weight. He then tried to bench press the weight. He could not move it. He tried 3 times with 10 seconds between each attempt. He still could not move it. Now he put on a nutrient holding device (U.S. Pat. Nos. 8,617,590, 9,636,310, 9,510,988) that was in the form of a band around a hat. He was now able to lift the weight once. On the second attempt he failed. Immediately he turned a switch which illuminated the light source device located near the umbilicus. He was then able to do the second repetition. On the third repetition tried immediately he failed. Then he switched on a vibrating module that was also located near the pubic area. Instantaneously, he was able to do the third repetition one time. Immediately he tried to do another repetition. He failed. He then put a magnetic module under his belt allowing the module to lie just below the umbilicus, he was then able to do yet another repetition.

This scenario was repeated. This time changing the order of the modalities. First the light source was used, then the nutrient holding device, then the magnetic module and finally the vibrating module. The results were the same.

The scenario was repeated. This time changing the order as follows. First the vibrating module was used, then the magnetic module, then the light source module and finally the nutrient holding device. The results were the same.

A subject determined his 1RM on the bench press. He rested 5 minutes. He then added 5 lbs. to his 1RM. He attempted to lift the weight. He could not move it. He tried again 3 times with 10 seconds between each attempt. He was still unsuccessful. Now he applied the four modalities at the same time. Now he is able to lift his 1RM plus 5 lbs. four times.

A subject determines his 1RM on a bench press. He is able to lift the weight one time but only one time. He waits 10 seconds. He tries to lift it again. He cannot. He then puts on a nutrient holding device as per U.S. Pat. No. 8,617,590. He tries again. This time he can lift the weight one time. He tries again after 10 seconds. He cannot lift the weight. He then presses a button which activates a light module over the umbilicus. Immediately, he is able to lift the weight another time. He then tries to lift the weight a second time. He cannot. Then, he switches on an electrical switch which activates a vibrating module set over the groin. Now he is able to lift the weight yet another time. He tries again after 10 seconds. He cannot lift the weight. Now he places a magnetic module under his belt located just below the umbilicus. He can now lift the weight yet another time.

A subject determines his one repletion max on a bench press. He tries to do a second repetition. He cannot. He then puts on a holding device containing nutrients (as per U.S. Pat. No. 8,617,590), a light source module with rays directed toward the skin, a magnetic module, and a vibrating module. He switches on both the vibrating and light module. Amazingly now he can lift the weight four more times.

Observations:
Using just the nutrient holding device (U.S. Pat. No. 8,617,590) the 1RP is increased from one repetition to two.
Using the nutrient holding device plus the light module the 1RM is increased from one repetition to three.
Using the nutrient holding device and the vibrating module the 1RM is increased from one repetition to three.
Using the nutrient holding device plus the magnetic module the 1RM is increased from one repetition to three.
Using the nutrient holding device with the vibrating module and the light source module the 1RM is increased from one repetition to four.
Using the nutrient holding device with the magnetic module and the light source module the 1RM is increased from one repetition to four.
Using the nutrient holding device with the magnetic module and vibrating module the 1RM is increased from one repetition to four.
Using the nutrient holding device with the magnetic module, the vibrating module, and the light source module the 1RM is increased from one repetition to five.

These above combinations represent an improvement to the patented invention U.S. Pat. No. 8,617,590.

The above combinations represent a synergistic effect in that the modalities work better when used together than when used separately.

The synergistic and surprising unexpected effect on muscle strength caused by the addition of a vibrating module and/or a light source module and/or the magnetic module to the nutrient holding device is immediate. By the click of a switch the subject's strength is instantly increased by just turning on the light module and/or the vibrating module on. Likewise. The synergistic effect of the magnetic module on muscle strength is immediate.

There is no need to have a pre work out or post work out therapeutic session for this device to work.

The effect on muscle strength is independent of the placement of the device. As demonstrated in the above examples, placement of the device distally from the muscle being tested can still positively effect muscle strength.

CONCLUSION

These illustrations of elastic belts are given as examples to explain the invention and not to limit the scope of this invention. Many holding devices are possible using these four modalities which can be used by themselves or working together synergistically in various combinations. By adjusting the length of the above elastic belts by various means the holding devices may be fashioned into headbands, wrist bands, and belts around the waist.

The resulting increase in muscle strength does translate into increase in athletic ability. Therefore, this increased athletic ability could be used to enhance sports apparel and equipment (hats, gloves, wrist bands, head bands, socks athletic shoes, helmets, uniforms, t shirts, sweatshirts etc.) These items themselves acting as holding devices containing these four modalities.

It is the contention of this invention that these four modalities: the light source module, the vibrating module, the magnetic module and the nutrient holding device all have the ability to balance acupuncture points resulting in increased muscle strength. As stated in U.S. Pat. No. 8,617,590 the amount and type of nutrients are chosen by the ability of the nutrients to stimulate reflex zones resulting in balanced acupuncture points resulting in increased muscle strength. The strength of the magnet is chosen by its ability to balance acupuncture points resulting in increased muscle strength. Likewise, the strength of the vibrating module measured in vibrations per second is determined by the ability of these vibrations to balance acupuncture points resulting in increased muscle strength. The strength of the LED light full spectrum light source is chosen by its ability to balance acupuncture points resulting in increased muscle strength. All four modalities have the ability to balance acupuncture points resulting in increased muscle strength A preferred embodiment of the invention may include magnetic module that has a magnet with 14600 Gauss, a light source with a power of 400 lumen, a vibratory module vibrating at 6000 to 7000 vibrations per minute, and a nutrient holding device that contains spirulina.

This increase in muscle strength is instantaneous. The addition of the light module and vibrating module and the magnetic module to the nutrient holding device has resulted in a surprising increase in muscle strength. The relationship of these four modalities to each other is one of synergy in that they perform better together than when used alone.

This invention works for weightlifters to lift more weight (become stronger). Then it would work for a batter to be able to hit the ball farther. It would work for a pitcher or quarter back be able to throw a ball faster and farther? A boxer would be able to hit harder using this device. A runner would be able to run faster using this device. A swimmer would be able to swim faster. A racehorse would also be stronger.

The invention claimed is:

1. An apparatus for providing increased muscle strength to a wearer, wherein the apparatus comprises:
   a vibration module, wherein the vibration module is configured to vibrate;
   a light source, wherein the light source is comprised of an LED light source;
   a sealed enclosure, wherein the sealed enclosure comprises a waterproof housing;
   wherein the sealed enclosure comprises a nutrient;
   wherein the nutrient comprises spirulina;
   a magnetic module; and a securing belt, wherein the securing belt comprises two fastening ends, an inner belt surface and an outer belt surface; when the securing belt forms a closed loop surrounding a central area when the fastening ends are connected; wherein the inner belt surface faces towards the central area of the closed loop when the two fastening ends are connected; wherein the outer belt surface faces away from the central area of the closed loop when the two fastening ends are connected;
   wherein the vibration module, the light source module, the sealed enclosure, and the magnetic module are attached to the inner belt surface;
   wherein the vibration module, the light source module and the magnetic module are attached across from the two fastening ends when the fastening ends are connected;
   wherein the light module is positioned above the vibration module on the securing belt; wherein the light module is positioned to apply light to the wearer's umbilicus area;
   wherein the vibration module is positioned to apply vibrations to the wearer's pubic area.

* * * * *